(12) United States Patent
Jarzynski

(10) Patent No.: US 9,028,395 B2
(45) Date of Patent: May 12, 2015

(54) SEXUAL STIMULATION DEVICES

(76) Inventor: Lori Jarzynski, Oconomowoc, WI (US)

( * ) Notice: Subject to any disclaimer, the term of this patent is extended or adjusted under 35 U.S.C. 154(b) by 345 days.

(21) Appl. No.: 13/590,824

(22) Filed: Aug. 21, 2012

(65) Prior Publication Data

US 2014/0058195 A1 Feb. 27, 2014

(51) Int. Cl.
*A61F 5/00* (2006.01)

(52) U.S. Cl.
CPC ............................... *A61F 5/00* (2013.01)

(58) Field of Classification Search
CPC ............... A61F 5/41; A61F 2005/414; A61F 2005/417; A61H 19/00; A61H 19/30; A61H 19/32; A61H 19/34; A61H 19/40; A61H 19/44; A61H 21/00
USPC ........................................................ 600/38–41
See application file for complete search history.

(56) References Cited

U.S. PATENT DOCUMENTS

| | | | | |
|---|---|---|---|---|
| 2,559,059 A * | 7/1951 | Worstenholm | ................... | 600/38 |
| 5,103,810 A * | 4/1992 | Chang | .............................. | 600/39 |
| 5,690,603 A * | 11/1997 | Kain | ................................ | 600/38 |
| 7,513,868 B1 * | 4/2009 | Fontenot | .......................... | 600/38 |
| 7,717,867 B2 * | 5/2010 | Nan | ................................ | 601/46 |
| 2009/0318755 A1* | 12/2009 | Adams et al. | ................... | 600/41 |

* cited by examiner

*Primary Examiner* — Samuel Gilbert
(74) *Attorney, Agent, or Firm* — Casimir Jones S.C.

(57) ABSTRACT

The present invention relates to a sexual stimulation device. In particular, the present invention relates to a sexual stimulation device having a phallic region, a discus region, and a handle region. In preferred embodiments, the device is configured for simultaneous insertion into a body cavity region (e.g., a vagina) and contacting of a non-body cavity region (e.g., a clitoris).

19 Claims, 3 Drawing Sheets

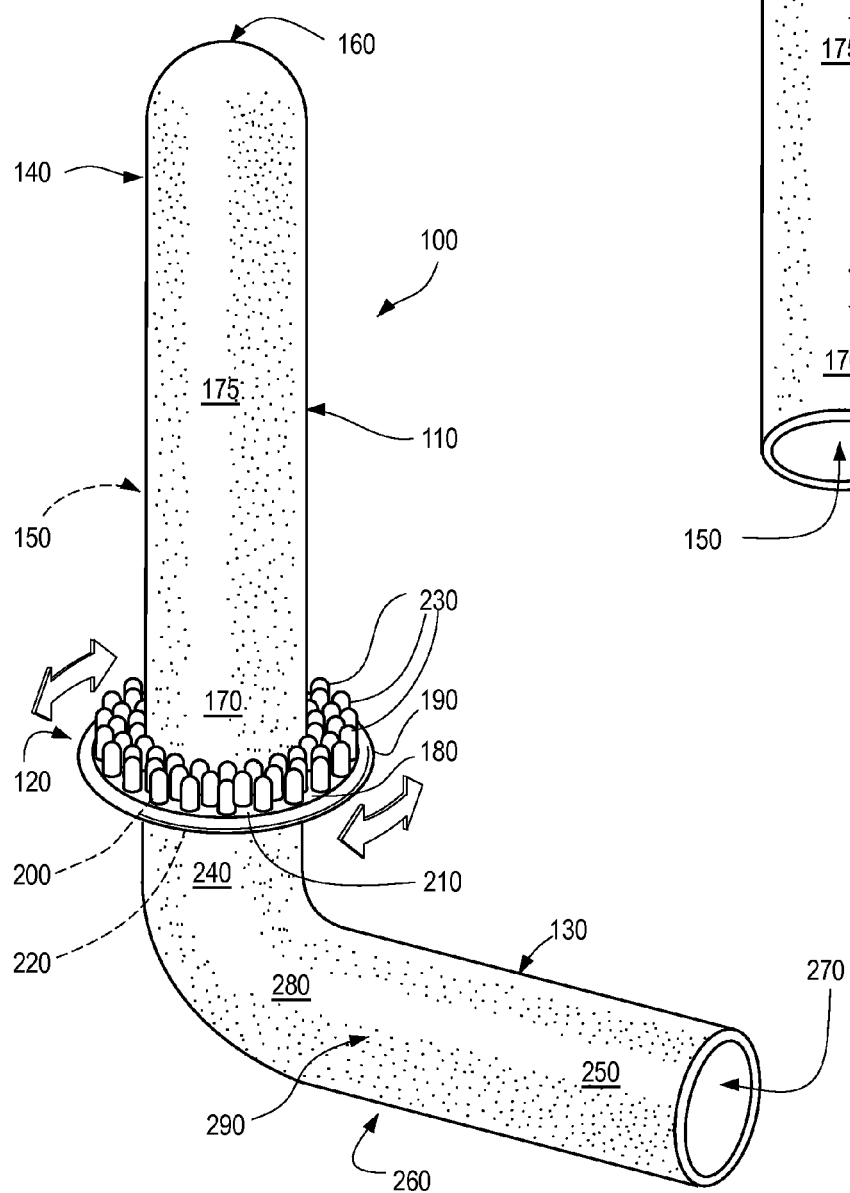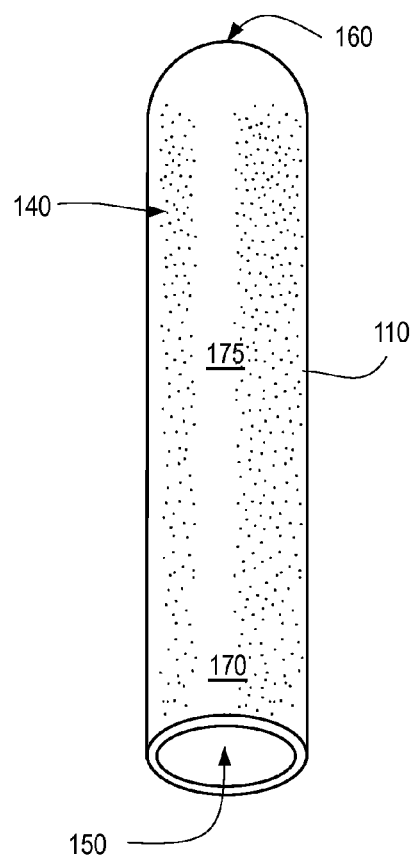

SEXUAL STIMULATION DEVICES

FIELD OF THE INVENTION

The present invention relates to a sexual stimulation device. In particular, the present invention relates to a sexual stimulation device having a phallic region, a discus region, and a handle region. In preferred embodiments, the device is configured for simultaneous insertion into a body cavity region (e.g., a vagina) and contacting of a non-body cavity region (e.g., a clitoris).

BACKGROUND

Historically there have been many prior art devices developed to improve or aid sexual gratification, both for men and women. For example, devices designed for use by women are typically phallic in form and may or may not include a vibration device within. Those without a vibrator are intended for vaginal penetration and stimulation while those that vibrate are also intended for vaginal penetration and stimulation and additionally for clitoral and G-spot stimulation. Although these phallic shaped devices may be used for clitoral stimulation during intercourse, they must be hand held at such times, which limits the possible positions and comfort of one or both partners. Also, during intercourse, such devices only stimulate locally and cannot stimulate the entire region surrounding the vagina.

Improved devices are needed.

SUMMARY OF THE INVENTION

The present invention overcomes the limitations of the prior art by providing devices that permit simultaneous stimulation of a body cavity region and a particular body region not within the body cavity region. In particular, the present invention provides devices having a phallic shaped region for stimulation of a body cavity region (e.g., a vagina) and discus region for stimulation of a non-body cavity region (e.g., a clitoris) wherein such simultaneous stimulation is not compromised with position adjustment (e.g., twisting) of the phallic shaped region.

Accordingly, in certain embodiments the present invention provides devices configured for sexual stimulation. The present invention is not limited to particular types of devices. In some embodiments, the devices comprise a phallic region and a discus region. The devices are not to particular types and/or kinds and/or size dimensions of the phallic and discus regions. In some embodiments, the phallic shaped region is configured for stimulation of a body cavity region (e.g., a vagina) and the discus region configured for stimulation of a non-body cavity region (e.g., a clitoris, labia), wherein such simultaneous stimulation is not compromised with position adjustment (e.g., twisting) of the phallic region.

In some embodiments, the phallic region has a cylindrical shape. In some embodiments, the phallic region has a phallic region proximal end and a phallic region distal end. In some embodiments, the phallic region has a length between approximately 1 and 24 inches and a width between approximately 1 and 4 inches. In some embodiments, the width of the phallic region is between 1 and 2 inches.

In some embodiments, the discus region has a circular shape. In some embodiments, the discus region has a discus region top face and a discus region bottom face. In some embodiments, the discus region has a diameter between 1.25 and 6 inches. In some embodiments, the discus region diameter is greater than the width of the phallic region. In some embodiments, the diameter of the discus region is between 1.5 and 3 inches.

In some embodiments, the discus region is configured to rotate around the phallic region proximal end. In some embodiments, the phallic region is engaged with the discus region such that the phallic region proximal end is positioned at the center of the discus region top face.

In some embodiments, the phallic region is positioned at the center of said discus region top face, wherein the discus region is adjustably positioned along the phallic region such that the discus region may be positioned at any position along the phallic region.

In some embodiments, the phallic region is configured to vibrate, thrust, and/or rotate. In some embodiments, the discus region is configured to vibrate.

In some embodiments, the discus region top face has thereon a plurality of discus region top face nodules. In some embodiments, the discus region top face nodules are cylindrical in shape. In some embodiments, the height of the discus region top face nodules are between 0.25 and 1 cm.

In some embodiments, the devices further comprise a handle region engaged with the discus region bottom face. In some embodiments, the handle region is L-shaped.

In some embodiments, the handle region has thereon a control region configured to permit a user to regulate various aspects of the device. For example, in some embodiments, the control region is configured to permit a user to regulate one or more of the following: the rotation speed of the discuss region, the rotation direction of the discus region, the vibration intensity of the discus region, the vibration intensity of the phallic region, the thrust intensity of the phallic region, the rotation speed of the phallic region, and the rotation direction of the phallic region.

In some embodiments, the device is battery powered. In some embodiments, the device is electricity powered.

In certain embodiments, the present invention provides methods for using such devices. For example, in some embodiments, the present invention provides methods for stimulating a woman wherein the phallic region is positioned inside a user's vagina while the discus region simultaneously contacts the clitoris of said woman. Twisting of the phallic region by the user does not impede the contacting of the clitoris by the discus region.

BRIEF DESCRIPTION OF THE DRAWINGS

FIG. 1 shows a side view of a device of the present invention.

FIG. 2 shows a lateral view of a phallic region of the present invention.

DETAILED DESCRIPTION

Figure 3A:
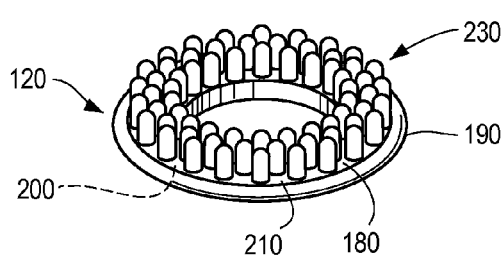
FIG. 3 shows A) an above lateral view of a discus region, and B) a below lateral view of a discus region.
FIG. 3C shows an embodiment wherein the discus region is approximately 50% circular.
FIG. 3D shows an embodiment wherein the discus region is approximately 25% circular.
Figure 3B:
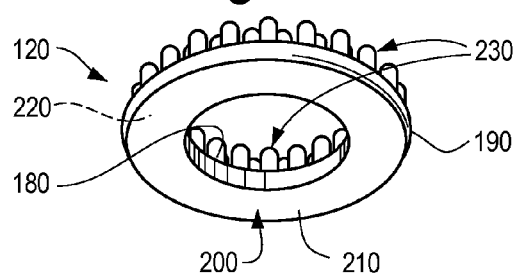
Figure 3C:
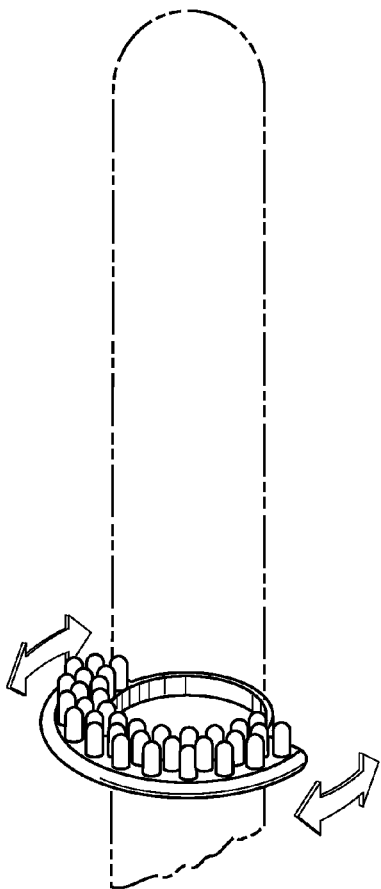
Figure 3D:
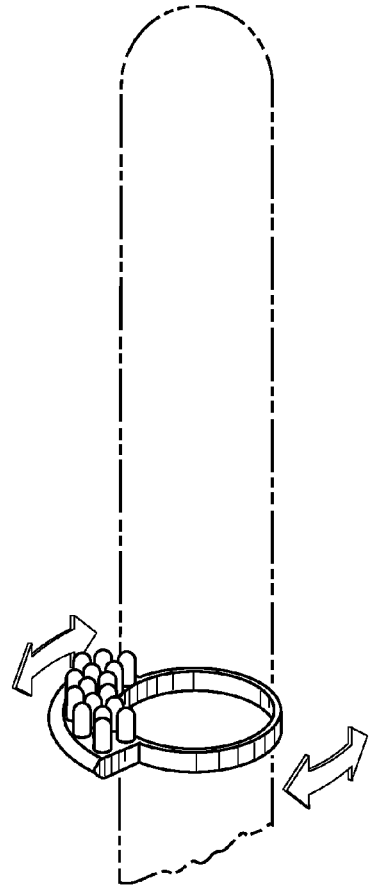

Numerous devices are commercially available which are configured to enhance sexual function and to provide sexual stimulation (see, e.g., U.S. Pat. Nos. 5,460,597, 5,725,473, 5,842,969, 6,099,463, 6,338,721, 6,422,993, 6,540,667, 6,749,557, 6,902,525, 6,997,888, 7,081,087, 7,166,072, 7,267,646, 7,530,944, 7,604,587, 7,658,707, 7,931,605, 7,993,262, 8,033,985, 8,047,984, and 8,171,575; U.S. Patent Application Publication Nos. 20020022761, 20020099261, 20020103415, 20030023139, 20040006291, 20040020241, 20040186344, 20050049453, 20050113636, 20050228219, 20050234292, 20060004251, 20060030750, 20060074273, 20060270897, 20070038019, 20070106109, 20070232967, 20080027275, 20090025133, 20090093856, 20090105528, 20090275796, 20090306468, 20090312599, 20100010292, 20100041944, 20100076257, 20100087703, 20100252052, 20100305483, 20110071445, 20110082332, 20110124959, 20110208231, 20120123199, and 20120143001; each herein incorporated by reference in its entirety). Examples include, but are not limited to, vibrators (e.g., penetrative vibrators, anal vibrators, G-spot vibrators, bullet vibrators, vibrator wands, rabbit vibrators), penile toys (e.g., artificial vaginas, cock rings, triple crowns, cock harnesses, ball locks, penis sleeves, docking sleeves), glass sex toys, nipple toys (e.g., nipple clamps, suction devices), anal toys (e.g., butt plugs, prostate massagers, anal beads), general penetrative toys (e.g., dildos).

The majority of these commercially available devices may be generally described as a dildo, i.e. a non-vibratory article adapted for either anal or vaginal insertion, or a vibrator, i.e. an article including a means for generating a vibration and/or rotation to enhance sexual stimulation.

Although dildos come in wide array of designs and styles they tend to be generally elongated and cylindrical in shape as this shape is best anatomically suited for vaginal and/or anal insertion.

Vibrators similarly come in wide array of designs and styles. Some types of vibrators are also elongated and cylindrical in shape so as to be anatomically suited for vaginal and/or anal insertion. Other types of vibrators are specifically designed for stimulation of a particular body region not within a body cavity (i.e., the region near the anterior junction of the labia minora, above the opening of the urethra and vagina (e.g., the clitoris)).

A limitation of such types of vibrators is that stimulation is limited to either the body cavity region or a particular body region not within the body cavity region. Some types of vibrators, however, have attempted to address this limitation. For example, the Rabbit vibrator (also known as "Jack Rabbit vibrator" or "Jessica Rabbit vibrator"), California Exotic Novelties, is a vibrating and rotating sex toy made in the shape of a phallus with a clitoral stimulator attached to the shaft. The Rabbit vibrator, accordingly, permits simultaneous stimulation of a body cavity region (e.g., a vagina) and a body region not within the body cavity region (e.g., a clitoris, labia minora and majora, vulva, perineum, etc.). A weakness with the Rabbit vibrator, however, is that the clitoral stimulator is positioned in a fixed manner. As such, presuming use with a woman, the design of the Rabbit vibrator is limited in that simultaneous stimulation of the vagina and clitoris requires stationary positioning of the device while it is being used. Indeed, in order to maintain such simultaneous stimulation, a user could not, for example, twist the phallus region as such twisting would terminate contact of the clitoral stimulator with the clitoris.

The present invention overcomes this limitation by providing devices that permit simultaneous stimulation of a body cavity region and a particular body region not within the body cavity region. In particular, the present invention provides devices having a phallic shaped region for stimulation of a body cavity region (e.g., a vagina) and rotating discus region for stimulation of a non-body cavity region (e.g., a clitoris, labia minora and majora, vulva, perineum, etc.) wherein such simultaneous stimulation is not compromised with position adjustment (e.g., twisting) of the phallic shaped region.

Accordingly, the present invention provides devices that permit simultaneous stimulation of a body cavity region and a particular body region not within the body cavity region. FIGS. 1-4 illustrate various preferred embodiments of the devices of the present invention. The present invention is not limited to these particular embodiments.

FIG. 1 shows a side view of a device 100 of the present invention. The device 100 is not limited to comprising particular regions and/or sections. In some embodiments, the device 100 comprises a phallic region 110, a discus region 120, and a handle region 130. The phallic region 110, discus region 120, and handle region 130 are not limited to a particular positional arrangement within the device 100. In some embodiments, as shown in FIG. 1, the phallic region 110 is connected with the discus region 120, and the handle region 120 is connected with the discus region 120. The device 100 is not limited to particular size dimensions. The device 100 is not limited to a particular use and/or function. In some embodiments, the device 100 is configured for insertion within a body cavity region (e.g., a vagina) with the phallic region 110 while simultaneously contacting (e.g., stimulating) a non-body cavity region (e.g., a clitoris, labia minora and majora, vulva, perineum, etc.) with the discus region 120, wherein such simultaneous insertion and contacting is not compromised upon positional adjustment (e.g., twisting) of phallic shaped region 110.

Still referring to FIG. 1, the phallic region 110 is not limited to a particular shape and/or size dimensions. In some embodiments, the shape of the phallic region 110 is cylindrical. In some embodiments, the shape of the phallic region 110 is rectangular. In some embodiments, the shape of the phallic region 110 is circular. In some embodiments, the shape of the phallic region 110 resembles an adult human penis. In some embodiments, the shape of the phallic region 110 is such that it is configured for insertion into any body cavity of a human being (e.g., an anal cavity, an oral cavity, a vagina). The phallic region 110 is not limited to particular size dimensions. In some embodiments, the size dimensions of the phallic region 110 is such that it is able to comfortably (e.g., without discomfort) (e.g., without tissue trauma) be inserted and maintained, and/or inserted and withdrawn from, for example, a vagina, an anal cavity, and/or an oral cavity. In some embodiments, the length of the phallic region 110 is approximately 5 inches (e.g. between 2 and 12 inches; between 3 and 11 inches; between 4 and 10 inches; between 5 and 9 inches; between 6 and 8 inches; between 6.5 inches and 7.5 inches; etc). In some embodiments, the length of the phallic region 110 is between 1 and 24 inches (e.g., between 22 inches and 2 inches; between 20 inches and 5 inches; between 15 and 8 inches; between 12 and 10 inches, etc.). In some embodiments, the phallic region 110 is cylindrical in shape. In some embodiments wherein the phallic region 110 is cylindrical in shape, the diameter (e.g., width) of the phallic region 110 is approximately 1.5 inches (e.g. between 2 and 12 inches; between 3 and 11 inches; between 4 and 10 inches; between 5 and 9 inches; between 6 and 8 inches; between 6.5 inches and 7.5 inches; etc). In some embodiments wherein the phallic region 110 is cylindrical in shape, the diameter (e.g., width) of the phallic region 110 is between approximately 1 and 6 inches (e.g., between 5.5 inches and 1.1 inches; between 4.5 inches and 1.25 inches; between 3 and 1.5 inches, etc.). The phallic region 110 is not limited to particular weight dimensions.

Still referring to FIG. 1, in some embodiments, the phallic region 110 has a phallic region exterior region 140, a phallic region interior region 150, a phallic region distal region 160 located near the tip of the phallic region 110, a phallic region proximal region 170 located near the base of the phallic region 110, and a phallic region mid-section region 175 located inbetween the phallic region proximal region 170 and the phallic region distal region 160.

Still referring to FIG. 1, in some embodiments, the phallic region exterior region 140 includes the exterior surface of the phallic region 110 that is designed to contact a user (e.g., contact a user's body cavity (e.g., a vagina)). In some embodiments, the phallic region interior region 150 is designed to not contact the user of the device 100. Indeed, in some embodiments, the phallic region interior region 150 is designed to have positioned within it machinery necessary to permit the phallic region 110 to vibrate, rotate, thrust, etc. (e.g., similar to, e.g., the Rabbit vibrator (also known as "Jack Rabbit vibrator" or "Jessica Rabbit vibrator"), California Exotic Novelties) (described in more detail below).

The phallic region 110 is not limited to a particular vibration location. In some embodiments, the entire phallic region 110 is configured to vibrate. In some embodiments, only the phallic region distal region 160 is configured to vibrate. In some embodiments, only the phallic region proximal region 170 is configured to vibrate. In some embodiments, only the phallic region mid-section region 175 is configured to vibrate.

The phallic region 110 is not limited to particular manner of rotation. In some embodiments, the entire phallic region 110 (e.g., the phallic region exterior region 140 and the phallic region interior region 150) is configured to rotate. In some embodiments, only the phallic region interior region 150 is configured to rotate. In some embodiments, the phallic region 110 is configured to rotate in continuous 360 degree rotation. In some embodiments, the phallic region 110 is configured to rotate in alternating 360 degree rotation (e.g., alternating clockwise and counter clockwise rotation). In some embodiments, the phallic region 110 is configured to rotate in random rotation (e.g., random clockwise and counter clockwise rotation; random degree rotation (e.g., 90 degree rotation, 180 degree rotation, 45 degree rotation, 270 degree rotation, 350 degree rotation, etc.). In some embodiments, the phallic region interior region 150 has therein "rotating beads" similar to, for example, the Rabbit vibrator (also known as "Jack Rabbit vibrator" or "Jessica Rabbit vibrator"), California Exotic Novelties.

The phallic region 110 is not limited to a particular type of thrust. In some embodiments, thrust refers to a repeating lateral extension and constriction of the phallic region (e.g., the entire phallic region; only a portion of the phallic region). The phallic region 110 is not limited to a particular thrust location. In some embodiments, the entire phallic region 110 is configured to thrust. In some embodiments, only the phallic region distal region 160 is configured to thrust. In some embodiments, only the phallic region proximal region 170 is configured to thrust. In some embodiments, only the phallic region mid-section region 175 is configured to thrust. In some embodiments, the entire phallic region 110 (e.g., the phallic region exterior region 140 and the phallic region interior region 150) is configured to thrust. In some embodiments, only the phallic region interior region 150 is configured to thrust. In some embodiments, the intensity (e.g., speed) of the thrusting can be adjusted by a user.

Still referring to FIG. 1, the phallic region 110 is not limited to a particular composition. In some embodiments, the composition of the phallic region exterior region 140 includes injection molded silicone. In some embodiments, the composition of the phallic region exterior region 140 includes any one or more or mixture of latex, CyberSkin (a thermal plastic elastomer), wood, rubber, glass, ceramic, fiberglass, metal (e.g., aluminum), Kevlar, any waterproof material, any type of plastic, etc. In some embodiments, the composition of the phallic region exterior region 140 is waterproof. In some embodiments, the composition of the phallic region exterior region 140 is any material or combination of materials that is not toxic upon contact with any tissue region (e.g., skin region) of a user of the device 100.

Still referring to FIG. 1, the phallic region 110 is not limited to a particular rigidity. In some embodiments, the rigidity of the phallic region 110 is non-flexible. In some embodiments, the rigidity of the phallic region 110 is flexible. In embodiments wherein the phallic region 110 is flexible, the degree of flexibility is not limited. In some embodiments wherein the phallic region 110 is flexible, the phallic region 110 may be flexible at one or more points along the plane of its length. In some embodiments wherein the phallic region 110 is flexible, the phallic region 110 has a memory such that upon release of a desired flexion, the phallic region 110 returns to its initial state. In some embodiments wherein the phallic region 110 is flexible, the degree of flexibility does not compromise the integrity of any machinery positioned within the phallic region interior region 150 (e.g., machinery to permit vibration, rotation, and/or thrusting of the phallic region 110 (described in more detail below)).

Still referring to FIG. 1, as noted above, in some embodiments the phallic region 110 is configured to vibrate, thrust, and/or rotate. The phallic region 110 is not limited to a particular manner of performing such vibration, thrusting, and/or rotation. In some embodiments, such vibration, thrusting, and/or rotation is performed via machinery positioned within the phallic region internal region 150. In some embodiments, such machinery positioned within the phallic region internal region 150 is further connected with additional regions of the device 100 (e.g., the handle region 130 and/or the discus region 120). The phallic region 110 is not limited to a particular manner of controlling such vibration, thrusting, and/or rotation. In some embodiments, such vibration, thrusting, and/or rotation is controlled by a user. In some embodiments, the device 100 has thereon controls for regulating the amount of vibration, thrusting, and/or rotation of the phallic region 110 that a user may modify. For example, in some embodiments, the handle region 130 has thereon a user region for manually regulating (e.g., increasing, decreasing) the amount of vibration, thrusting, and/or rotation of the phallic region 110 (described in more detail below). The phallic region 110 is not limited to particular degrees of vibration, thrusting, and/or rotation. In some embodiments, the degree (e.g. frequency, intensity, speed, etc.) of vibration, thrusting, and/or rotation within the phallic region 110 is such that it does not cause bodily harm (e.g., tissue trauma, etc.) to a user. In some embodiments, the degree of vibration, thrusting, and/or rotation of the phallic region 110 is similar to products presently available on the open market.

FIG. 2 shows a lateral view of a phallic region 110 of the present invention. As shown, the phallic region exterior region 140 has a cylindrical shape. The phallic region interior region 150 is shown near the phallic region proximal region 170. The phallic region distal region 160 is shown near the tip of the phallic region 110. The phallic region mid-section region 175 is shown inbetween the phallic region proximal region 170 and the phallic region distal region 160.

Referring again to FIG. 1, the discus region 120 is not limited to a particular size dimension and/or shape. In some embodiments, the size dimension and/or shape of the discus region 120 is such that it permits a user to simultaneously contact a non-body cavity region (e.g., a clitoris, labia minora and majora, vulva, perineum, etc.) with the discus region 120 while the phallic region 110 is inserted into a body cavity region (e.g., a vagina), wherein such simultaneous insertion and contacting is not compromised upon positional adjustment (e.g., twisting) of phallic shaped region 110.

Still referring to FIG. 1, the discus region 120 is not limited to a particular shape. In some embodiments, the shape of the discus region 120 is rectangular, oval, triangular, etc. In some embodiments, as shown in FIG. 1, the shape of the discus region 120 is circular. In some embodiments wherein the shape of the discus region 120 is circular, the discus region 120 is 100% circular. In some embodiments wherein the shape of the discus region 120 is circular, the discus region 120 is 50% circular. In some embodiments wherein the shape of the discus region 120 is circular, the discus region 120 is 25% circular. In some embodiments wherein the shape of the discus region 120 is circular, the discus region 120 is 75% circular. In some embodiments, as shown in FIG. 1, the discus region 120 has a discus region top face 180, a discus region mid-region face 190, and a discus region bottom face 200.

Still referring to FIG. 1, the discus region 120 is not limited to a positional relationship with the phallic region 110 and the handle region 130. In some embodiments, the discus region 120 is integrated with phallic region 110 such that the phallic region proximal region 170 engages with the discus region top face 180. In some embodiments, the discus region 120 is integrated with phallic region 110 such that the phallic region proximal region 170 engages with the discus region top face 180 such that the discus region top face 180 is evenly spaced around the phallic region 110. In some embodiments, the handle region 130 is integrated with the discus region bottom face 200 (described in more detail below).

Still referring to FIG. 1, the discus region 120 is not limited to particular size dimensions. In some embodiments, the size of the discus region 120 is such that it is able to comfortably contact a desired non-body cavity region (e.g., a clitoris, labia minora and majora, vulva, perineum, etc.) while the phallic region 110 is positioned in a body cavity region (e.g., a vagina). In some embodiments wherein the discus region 120 is circular in shape, the discus region 120 is approximately 2.5 inches in diameter (e.g., 0.1 inches in diameter, 0.25 inches in diameter, 0.5 inches in diameter, 0.75 inches in diameter, 1.0 inch in diameter, 1.25 inches in diameter, 1.5 inches in diameter, 1.75 inches in diameter, 2.0 inches in diameter, 3 inches in diameter, 5 inches in diameter, etc.). In some embodiments wherein the discus region 120 is circular in shape, the discus region 120 is approximately between 1 and 6 inches in diameter (e.g., between 1.5 and 5 inches; between 1.75 and 4 inches; between 2 and 4.5 inches; between 2.25 and 4 inches; etc.). In some embodiments, the diameter of the discus region is greater than the width of phallic region. In some embodiments wherein the discus region 120 is circular in shape, the distance from the edge of the discus region top face 180 to the phallic region proximal region 170 is approximately 0.5 inches (e.g., 0.1 inches, 0.25 inches, 0.4 inches, 0.45 inches, 0.5 inches, 0.55 inches, 0.75 inches, 1 inch, 1.1 inches, 1.5 inches, 2.0 inches, etc.). In some embodiments, the height of the discus region mid-region face 190 is approximately 0.5 cm (e.g., 0.1 cm, 0.2 cm, 0.3 cm, 0.4 cm, 0.45 cm, 0.5 cm, 0.55 cm, 0.6 cm, 0.7 cm, 1 cm, 1.1 cm, 1.5 cm, 2.5 cm, etc.).

Still referring to FIG. 1, the discus region 120 has a discus region exterior region 210 and a discus region interior region 220. In some embodiments, the discus region exterior region 210 includes the exterior surface of the discus region 120 that is designed to contact a user (e.g., contact a user's non-body cavity (e.g., a clitoris)). In some embodiments, the discus region interior region 220 is designed to not contact the user of the device 100. Indeed, in some embodiments, the discus region interior region 220 is designed to have positioned within it machinery necessary to permit the discus region 120 to vibrate and/or rotate (described in more detail below). The discus region 120 is not limited to a particular vibration location. In some embodiments, the entire discus region 120 is configured to vibrate. In some embodiments, only the discus region top face 180 is configured to vibrate. In some embodiments, only the discus region top face nodules (described in more detail below) are configured to vibrate. The discus region 120 is not limited to particular manner of rotation. In some embodiments, the discus region 120 is configured to rotate in continuous 360 degree rotation. In some embodiments, the discus region 120 is configured to rotate in alternating 360 degree rotation (e.g., alternating clockwise and counter clockwise rotation). In some embodiments, the discus region 120 is configured to rotate in random rotation (e.g., random clockwise and counter clockwise rotation; random degree rotation (e.g., 90 degree rotation, 180 degree rotation, 45 degree rotation, 270 degree rotation, 350 degree rotation, etc.).

Still referring to FIG. 1, the discus region exterior region 210 is not limited to a particular composition. In some embodiments, the composition of the discus region exterior region 210 includes injection molded silicone. In some embodiments, the composition of the discus region exterior region 210 includes any one or more or mixture of latex, CyberSkin (a thermal plastic elastomer), wood, rubber, glass, ceramic, fiberglass, metal (e.g., aluminum), Kevlar, any waterproof material, any type of plastic, etc. In some embodiments, the composition of the discus region exterior region 210 is waterproof. In some embodiments, the composition of the discus region exterior region 210 is any material or combination of materials that is not toxic upon contact with any tissue region (e.g., skin region) of a user of the device 100.

Still referring to FIG. 1, the discus region 120 is not limited to a particular rigidity. In some embodiments, the rigidity of the discus region 120 is non-flexible. In some embodiments, the rigidity of the discus region 120 is flexible. In embodiments wherein the discus region 120 is flexible, the degree of flexibility is not limited. In some embodiments wherein the discus region 120 is flexible, the discus region 120 has a memory such that upon release of a desired flexion, the discus region 120 returns to its initial state. In some embodiments wherein the discus region 120 is flexible, the degree of flexibility does not compromise the integrity of any machinery positioned within the discus region interior region 220 (e.g., machinery to permit vibration and/or rotation of the discus region 120 (described in more detail below)).

Still referring to FIG. 1, in some embodiments, the discus region top face 180 has thereon a plurality of discus region top face nodules 230. The device 100 is not limited to particular size dimensions and/or shapes for the discus region top face nodules 230. In some embodiments, the shape and size dimensions of the discus region top face nodules 230 is such that a user can detect a sensation (e.g., feeling) upon contact with a non-body cavity region (e.g., a clitoris). The discus region top face 180 is not limited having a particular amount of discus region top face nodules 230 positioned thereon (e.g., 100% of the discus region top face 180 is covered with discus region top face nodules 230; 99%; 97%; 95%; 92.5%; 90%; 80%; 75%; 60%; 50%; 30%; 20%; 10%; 5%; 1%; 0.5%; etc.). In some embodiments wherein less than 100% of the discus region top face 180 has discus region top face nodules 230 positioned thereon, the discus region top face nodules 230 are evenly spaced apart. In some embodiments wherein less than 100% of the discus region top face 180 has discus region top face nodules 230 positioned thereon, the discus region top face nodules 230 are randomly spaced apart.

Still referring to FIG. 1, the discus region top face nodules 230 are not limited to a particular shape. In some embodiments, the shape of the discus region top face nodules 230 are cylindrical. In some embodiments, the shape of the discus region top face nodules 230 are rectangular. In some embodiments, the shape of the discus region top face nodules 230 are circular. In some embodiments, the shape of the discus region top face nodules 230 are such that each is configured to contact any non-body cavity of a human being (e.g., a clitoris) without causing bodily discomfort and/or trauma. The discus region top face nodules 230 are not limited to particular size dimensions. In some embodiments, the height of the discus region top face nodules 230 are approximately 0.75 inches (e.g., 0.1 inches; 0.2 inches; 0.25 inches; 0.5 inches; 0.6 inches; 0.7 inches; 0.8 inches; 1 inch; 1.1 inches; 1.25 inches; 2.0 inches; 5 inches, etc.). In some embodiments, the height of the discus region top face nodules 230 are between 0.25 and 1 cm (e.g., between approximately 0.3 cm and 0.9 cm; between approximately 0.4 cm and 0.8 cm; between approximately 0.5 cm and 0.75 cm; between approximately 0.6 cm and 0.7 cm; etc.). In some embodiments, the width of the discus region top face nodules 230 are approximately 0.5 cm (e.g., 0.05 cm; 0.1 cm; 0.2 cm; 0.35 cm; 0.4 cm; 0.47 cm; 0.52 cm; 0.6 cm; 0.75 cm; 0.8 cm; 1 cm; 2.5 cm; 5 cm; etc.). The discus region top face nodules 230 are not limited to particular weight dimensions.

Still referring to FIG. 1, the discus region top face nodules 230 are not limited to a particular composition. In some embodiments, the composition of the discus region top face nodules 230 includes injection molded silicone. In some embodiments, the composition of the discus region top face nodules 230 includes any one or more or mixture of latex, CyberSkin (a thermal plastic elastomer), wood, rubber, glass, ceramic, fiberglass, metal (e.g., aluminum), Kevlar, any waterproof material, any type of plastic, etc. In some embodiments, the composition of the discus region top face nodules 230 is waterproof. In some embodiments, the composition of the discus region top face nodules 230 includes any material or combination of materials that is not toxic upon contact with any tissue region (e.g., skin region) of a user of the device 100.

Still referring to FIG. 1, as noted above, in some embodiments the discus region 120 is configured to vibrate and/or rotate. The discus region 120 is not limited to a particular manner of performing such vibration and/or rotation. In some embodiments, such vibration and/or rotation is performed via machinery positioned within the discus region internal region 220. In some embodiments, such machinery positioned within the discus region internal region 220 is further connected with additional regions of the device 100 (e.g., the handle region 130 and/or the phallic region 110). The discus region 120 is not limited to a particular manner of controlling such vibration and/or rotation. In some embodiments, such vibration and/or rotation is controlled by a user. In some embodiments, the device 100 has thereon controls for regulating the amount of vibration and/or rotation of the discus region 120 that a user may modify. For example, in some embodiments, the handle region 130 has thereon a user region for manually regulating (e.g., increasing, decreasing) the amount of vibration and/or rotation of the discus region 120 (described in more detail below). The discus region 120 is not limited to particular degrees of vibration and/or rotation. In some embodiments, vibration of the discus 120 results in vibration of the discus region top face nodules 230. In some embodiments, the degree (e.g. frequency, intensity, speed, etc.) of vibration and/or rotation within the discus region 120 is such that it does not cause bodily harm (e.g., tissue trauma, etc.) to a user.

In some embodiments, the position of the discus region in relation to the phallic region may be adjusted. For example, in some embodiments, the phallic region is positioned at the center of said discus region top face, wherein the discus region is adjustably positioned along the phallic region such that the discus region may be positioned at any position along said phallic region (near or at the phallic region proximal end, near or at the phallic region distal end, near or at the phallic region mid section). In such embodiments, a user may insert the phallic region into a body cavity (e.g., a vagina) a distance that is not a full amount (e.g., not the full length of the phallic region) while still having the discus region contact a non-body cavity region (e.g., a clitoris). For example, a user may insert the phallic region a distance less than 100% of the length of the phallic region shaft (e.g., 1%, 5%, 10%, 25%, 35%, 50%, 70%, 80%, 85%, 90%, 95%) and, through adjustment of the position of the discus region position along the phallic region, simultaneously contact a non-body cavity region (e.g., a clitoris). In addition, for example, in some embodiments, the device is configured such that a user may manually move the discus region to a desired location along the phallic region shaft. For example, in some embodiments, the device is configured such that the discus region is positioned at the distal end of the phallic region, and upon insertion of the phallic region into a body cavity (e.g., a vagina), the discus region moves down the shaft in a manner consistent with the depth of insertion of the phallic region into the body cavity (e.g., thereby ensuring contact of the discus region with the non-body cavity region (e.g., clitoris) regardless of the depth of insertion of the phallic region into a body cavity). In such embodiments, as a phallic region is withdrawn, the discus region also adjusts in position along the phallic shaft accordingly. Indeed, in such embodiments, the device is still able to simultaneously stimulate a body cavity region (e.g., a vagina) while contacting a non-body cavity region (e.g., a clitoris, labia, etc.), regardless of how deep the phallic region may be inserted into such a body cavity.

FIG. 3 shows A) an above lateral view of a discus region and B) a below lateral view of a discus region. As shown, the shape of the discus region 120 is circular, having a discus region mid-region face 190 is located below the discus region top face 180 and above the discus region bottom face 200. As shown, the discus region top face 180 has thereon discus region top face nodules 230. As shown, the discus region top face nodules 230 are cylindrical in shape and are evenly spaced on the discus region top face 180. FIG. 3C shows an embodiment wherein the discus region is approximately 50% circular. FIG. 3D shows an embodiment wherein the discus region is approximately 25% circular.

Referring again to FIG. 1, the handle region 130 is not limited to a particular size dimension and/or shape. In some embodiments, the size dimension and/or shape of the handle region 130 is such that it permits a user to grasp the handle region 130 while simultaneously contacting a non-body cavity region (e.g., a clitoris, labia minora and majora, vulva, perineum, etc.) with the discus region 120 and inserting the phallic region 110 into a body cavity region (e.g., a vagina), wherein such simultaneous insertion and contacting is not compromised upon positional adjustment (e.g., twisting) of phallic shaped region 110.

Still referring to FIG. 1, the handle region 130 is not limited to a particular shape. In some embodiments, the shape of the handle region 130 is L-shaped, cylindrical, rectangular, oval, etc. In some embodiments, as shown in FIG. 1, the shape of the handle region 130 is L-shaped. In some embodiments, the handle region 130 has a handle region distal region 240 and a handle region proximal region 250. In some embodiments, the handle region 130 has a handle region exterior region 260 and a handle region interior region 270.

In some embodiments wherein the handle region 130 is L-shaped, the handle region 130 has a handle region bend region 280 and a handle region main shaft 290. In some embodiments wherein the handle region 130 is L-shaped, the degree of bend at the interface of the handle region bend region 280 and the handle region main shaft 290 is not limited (e.g., 10 degree bend; 20 degree bend; 45 degree bend; 60 degree bend; 70 degree bend; 90 degree bend; 110 degree bend; 120 degree bend; 150 degree bend; 175 degree bend). In some embodiments wherein the handle region 130 is L-shaped, as shown in FIG. 1, the degree of bend at the interface of the handle region bend region 280 and the handle region main shaft 290 is 90 degrees. In some embodiments wherein the handle region 130 is L-shaped, the degree of bend at the interface of the handle region bend region 280 and the handle region main shaft 290 is adjustable by a user to achieve a desired bend (e.g., adjustable to a 45 degree bend at the interface of the handle region bend region 280 and the handle region main shaft 290; adjustable to 60 degree bend; 90 degree bend; 12 degree bend; 150 degree bend).

Still referring to FIG. 1, the handle region 130 is not limited to a positional relationship with the phallic region 110 and the discus region 130. In some embodiments, the handle region 130 is integrated with the discus region 120 such that the handle region distal region 240 engages the discus region bottom face 200.

Still referring to FIG. 1, the handle region 130 is not limited to particular size dimensions. In some embodiments, the size of the handle region 120 is such that it permits a user to grasp the handle region 130 while simultaneously contacting a non-body cavity region (e.g., a clitoris, labia minora and majora, vulva, perineum, etc.) with the discus region 120 and inserting the phallic region 110 into a body cavity region (e.g., a vagina), wherein such simultaneous insertion and contacting is not compromised upon positional adjustment (e.g., twisting) of phallic shaped region 110. In some embodiments, the width of the handle region 130 is approximately 1.5 inches (e.g., 0.25 inches; 0.5 inches; 0.6 inches; 0.75 inches; 1 inch; 1.1 inches; 1.25 inches; 1.45 inches; 1.55 inches; 1.6 inches; 1.75 inches; 1.9 inches; 2.5 inches; 2.6 inches; 2.8 inches; 3.25 inches; etc). In some embodiments wherein the handle region 130 is cylindrical in shape, the length of the handle region 130 is approximately 6 inches (e.g.; 1 inch; 2 inches; 2.5 inches; 3 inches; 4.5 inches; 5 inches; 5.5 inches; 7 inches; 7.5 inches; 9 inches; etc.). In some embodiments wherein the handle-region is L-shaped, the length of the handle region bend region 280 is approximately 2.5 inches (e.g., 1 inch; 1.5 inches; 1.6 inches; 1.75 inches; 1.85 inches; 2.0 inches; 2.15 inches; 2.25 inches; 2.4 inches; 2.55 inches; 2.65 inches; 2.75 inches; 3 inches; 3.25 inches; 3.5 inches; 4.5 inches; 6 inches; etc.). In some embodiments wherein the handle-region is L-shaped, the length of the handle region main shaft 290 is approximately 4.5 inches (e.g., 3 inches; 3.5 inches; 3.9 inches; 4.25 inches; 4.4 inches; 4.6 inches; 4.75 inches; 4.9 inches; 5 inches; 5.25 inches; 6 inches; 7.5 inches; 9 inches etc.).

Still referring to FIG. 1, the handle region exterior region 260 includes the exterior surface of the handle region 130 that is designed to contact a user (e.g., contact a user's hand). The handle region exterior region 260 is not limited to a particular composition. In some embodiments, the composition of the handle region exterior region 260 includes injection molded silicone. In some embodiments, the composition of the handle region exterior region 260 includes any one or more or mixture of latex, CyberSkin (a thermal plastic elastomer), wood, rubber, glass, ceramic, fiberglass, metal (e.g., aluminum), Kevlar, any waterproof material, any type of plastic, etc. In some embodiments, the composition of the handle region exterior region 260 is waterproof. In some embodiments, the composition of the handle region exterior region 260 is any material or combination of materials that is not toxic upon contact with any tissue region (e.g., skin region) of a user of the device 100.

Still referring to FIG. 1, in some embodiments, the handle region interior region 270 is designed to not contact the user of the device 100. Indeed, in some embodiments, the handle region interior region 270 is designed to have positioned within it machinery necessary to permit the discus region 120 to vibrate and/or rotate, and/or permit the phallic region 110 to vibrate, rotate, expand and/or contact. The handle region 130 is not limited to a particular type of machinery necessary to permit the discus region 120 to vibrate and/or rotate, and/or permit the phallic region 110 to vibrate, rotate, expand and/or contact. Indeed, the machinery necessary to permit the discus region 120 to vibrate and/or rotate, and/or permit the phallic region 110 to vibrate, rotate, and/or thrust is well known in the art. In some embodiments, the handle region interior region 270 is sized to permit not only the machinery necessary to permit the discus region 120 to vibrate and/or rotate, and/or permit the phallic region 110 to vibrate, rotate, expand and/or contact, but also fit an energy means to run such machinery (e.g., any sized battery source; a plug source; etc.). In some embodiments, the handle region 130 is configured to permit a user to access the handle region interior region 270 (e.g., for purposes of accessing the machinery necessary to permit the discus region 120 to vibrate and/or rotate, and/or permit the phallic region 110 to vibrate, rotate, expand and/or contact) (e.g., for purposes of accessing replacing a battery). In some embodiments, a user is able to access the handle region interior region 270 at the handle region proximal region 250. In some embodiments, a user is able to access the handle region interior region 270 at the handle region proximal region 240. In some embodiments wherein the handle is L-shaped, a user is able to access the handle region interior region 270 at the handle region bend region 280.

Still referring to FIG. 1, the handle region 130 has thereon a handle region setting region 290 for purposes of allowing a user to manually control the machinery necessary to permit the discus region 120 to vibrate and/or rotate, and/or permit the phallic region 110 to vibrate, rotate, and/or thrust. For example, in some embodiments, manual control of the handle region setting region 290 by a user permits a user to control the rotation of the discus region 120 (e.g., the speed of rotation, the direction of rotation (e.g., clockwise, counter-clockwise, random), the intensity of vibration of the discus region 120, the rotation of the phallic region 110 (e.g., the speed of rotation, the direction of rotation (e.g., clockwise, counter-clockwise, random), the vibration intensity of the phallic region 110, and/or the thrusting intensity of the phallic region 110. The handle region setting region 290 is not limited to particular type of machinery to permit a user to manually control the machinery necessary to permit the discus region 120 to vibrate and/or rotate, and/or permit the phallic region 110 to vibrate, rotate, and/or thrust. Indeed, the machinery necessary to permit a user to manually control the machinery necessary to permit the discus region 120 to vibrate and/or rotate, and/or permit the phallic region 110 to vibrate, rotate, and/or thrust is well known in the art.

In some embodiments, the device is battery powered. In some embodiments, the device is electricity powered.

Figure 4:
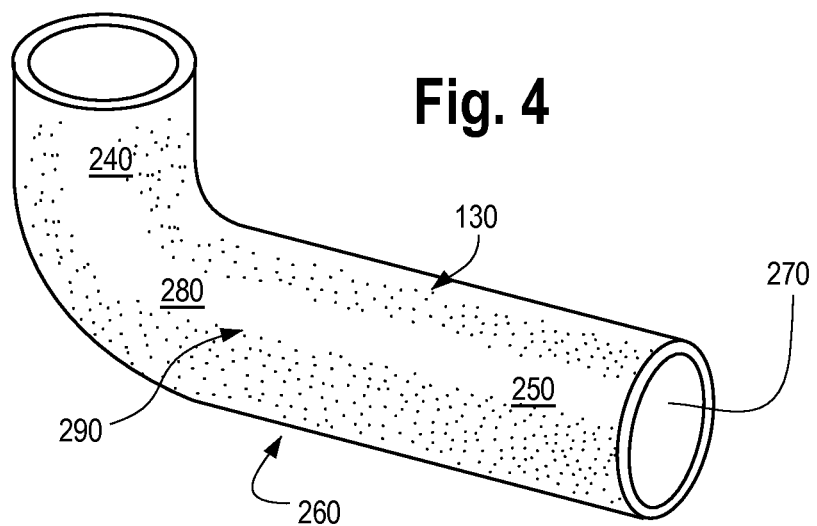
FIG. 4 shows a lateral view of an L-shaped handle region.

FIG. 4 shows a lateral view of an L-shaped handle region 130. The handle region 130 is shown having a handle region distal region 240, handle region proximal region 250, handle region exterior region 260, handle region interior region 270, the handle region bend region 280, handle region main shaft 290.

In some embodiments, the device has thereon two phallic regions and discus regions connected to a handle region. Such a design permits, for example, the simultaneous insertion of the device into two body cavity regions (e.g., a vagina and an anal cavity). Such a design permits, for example, the simultaneous insertion of the device into a body cavity region of one user and a body cavity region of a second user. Such a design permits, for example, the simultaneous insertion of the device into two different body cavity regions of one user.

The devices of the present invention are not limited to particular uses. In some embodiments, the devices of the present invention are used for insertion into anal cavities. In some embodiments, the devices are used for insertion into oral cavities. In some embodiments, the devices are used for simultaneous stimulation of a woman's vagina and clitoris, wherein such simultaneous stimulation is not affected by the twisting of the device. Indeed, the devices of the present invention overcome the limitations of the "rabbit" devices are a user is able to simultaneously stimulate the vagina and clitoris while rotating the phallic region.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in the relevant fields are intended to be within the scope of the present invention.

I claim:

1. A device comprising a phallic region and a discus region,
    the phallic region having a cylindrical shape, the phallic region having a phallic region proximal end, a phallic region distal end, a phallic region exterior region, and a phallic region internal region,
    the phallic region having a length between approximately 1 and 24 inches and a width between approximately 1 and 4 inches,
    the discus region having a circular shape, the discus region having a discus region top face, a discus region bottom face, a discus region external region, and a discus region internal region,
    the discus region having a diameter between 1.25 and 6 inches, the discus region diameter is greater than the width of the phallic region,
    the phallic region positioned within a center of the discus region top face such that the discus region is evenly spaced around the phallic region,
    wherein the discus region is adjustably positioned along the phallic region such that the discus region may be positioned at any position along the phallic region,
    wherein the discus region interior region has therein machinery configured to rotate the discus region around the phallic region.

2. The device of claim 1, further comprising a handle having a handle region exterior region and a handle region interior region, wherein the handle is engaged with the discus region bottom face.

3. The device of claim 2, wherein the handle region exterior region has thereon a handle region setting region configured for controlling the machinery configured to rotate the discus region around the phallic region, wherein the controlling adjusts rotation speed of the discus region around the phallic region.

4. The device of claim 2, wherein the handle region interior region has therein machinery connected with the machinery in the discus region interior region configured to rotate the discus region around the phallic region.

5. The device of claim 4, wherein the handle region exterior region has thereon a handle region setting region configured for controlling the machinery within the handle interior region connected with the machinery within the discus region configured to rotate the discus region around the phallic region, wherein the controlling adjusts rotation speed of the discus region around the phallic region.

6. The device of claim 4, wherein the handle region exterior region has thereon a handle region setting region configured for controlling the machinery within the phallic region interior region connected with the machinery within the discus region configured to rotate the discus region around the phallic region, wherein the controlling adjusts rotation speed of the discus region around the phallic region.

7. The device of claim 2, wherein the phallic region interior region has therein machinery connected with the machinery in the discus region interior region configured to rotate the discus region around the phallic region.

8. The device of claim 2,
    wherein the phallic region interior region has therein machinery connected with the machinery in the discus region interior region configured to rotate the discus region around the phallic region,
    wherein the handle region interior region has therein machinery connected with the machinery in the discus region interior region configured to rotate the discus region around the phallic region.

9. The device of claim 8, wherein the machinery within the phallic region interior region is connected with the machinery within the handle interior region.

10. The device of claim 9, wherein the handle region exterior region has thereon a handle region setting region configured for controlling a) the machinery within the phallic region interior region connected with the machinery within the discus region configured to rotate the discus region around the phallic region and the machinery within the handle interior region, b) the machinery within the handle interior region connected with the machinery within the discus region configured to rotate the discus region around the phallic region and the machinery within the phallic region interior region, and c) the machinery within the discus region configured to rotate the discus region around the phallic region connected with the machinery within the phallic region interior region and the machinery within the handle interior region.

11. The device of claim 2, wherein said handle region is L-shaped.

12. The device of claim 1, wherein the controlling adjusts the rotation speed of the discus region around the phallic region.

13. The device of claim 1, wherein said phallic region is configured to vibrate, thrust, and/or rotate.

14. The device of claim 1, wherein said discus region top face has thereon a plurality of discus region top face nodules.

15. The device of claim 14, wherein said discus region top face nodules are cylindrical in shape, wherein a height of said discus region top face nodules are between 0.25 and 1 cm.

16. The device of claim 1,
    wherein the width of said phallic region is between 1 and 2 inches, wherein the diameter of said discus region is between 1.5 and 3 inches.

17. The device of claim 1, wherein said discus region is configured to vibrate.

18. A device comprising a handle, a phallic region, and a discus region,
- the phallic region having a cylindrical shape, the phallic region having a phallic region proximal end, a phallic region distal end, a phallic region exterior region, and a phallic region internal region, wherein said phallic region is configured to vibrate, thrust, and rotate,
- the phallic region having a length between approximately 1 and 24 inches and a width between approximately 1 and 4 inches,
- the discus region having a circular shape, the discus region having a discus region top face, a discus region bottom face, a discus region external region, and a discus region internal region,
- the handle having a handle region exterior region and a handle region interior region, wherein the handle is engaged with the discus region bottom face,
- the discus region having a diameter between 1.25 and 6 inches, the discus region diameter greater than the width of the phallic region,
- the phallic region positioned within a center of the discus region top face such that the discus region is evenly spaced around the phallic region,
- wherein the discus region is adjustably positioned along the phallic region such that the discus region may be positioned at any position along the phallic region,
- wherein the discus region interior region has therein machinery configured to rotate the discus region around the phallic region,
- wherein the handle region interior region has therein machinery connected with the machinery in the discus region interior region configured to rotate the discus region around the phallic region,
- wherein the handle region exterior region has thereon a handle region setting region configured for controlling the machinery within the handle interior region connected with the machinery within the discus region configured to rotate the discus region around the phallic region, wherein the controlling adjusts rotation speed of the discus region around the phallic region.

19. The device of claim 18, wherein said discus region is configured to vibrate.

* * * * *